(12) United States Patent
Honma

(10) Patent No.: US 6,568,243 B1
(45) Date of Patent: May 27, 2003

(54) METHOD OF EVALUATING CAPACITANCE VALUE OF CAPACITOR ON SEMICONDUCTOR SUBSTRATE

(75) Inventor: Ichiro Honma, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/253,027

(22) Filed: Feb. 19, 1999

(30) Foreign Application Priority Data

Feb. 19, 1998 (JP) .......................................... 10-037454

(51) Int. Cl.⁷ .......................... G01N 19/02; G01R 27/26
(52) U.S. Cl. .............................................. 73/9; 324/662
(58) Field of Search .............................. 73/104, 105, 9, 73/37, 159, 198, 633; 188/1.11; 324/658, 662

(56) References Cited

U.S. PATENT DOCUMENTS

| | | | | |
|---|---|---|---|---|
| 4,051,713 A | * | 10/1977 | Bao et al. ...................... | 73/663 |
| 4,213,331 A | * | 7/1980 | Porter .......................... | 73/105 |
| 4,270,390 A | * | 6/1981 | Kimball et al. ............... | 73/663 |
| 4,765,181 A | * | 8/1988 | Numoto et al. ............... | 73/105 |
| 4,986,109 A | * | 1/1991 | Moon ............................... | 73/7 |
| 5,145,533 A | * | 9/1992 | Yoshitomi et al. ............ | 73/104 |
| 5,450,746 A | * | 9/1995 | Howard ........................ | 73/105 |
| 5,756,885 A | * | 5/1998 | Poku et al. ................... | 73/104 |
| 5,859,357 A | * | 1/1999 | Kameyama et al. ............. | 73/9 |

FOREIGN PATENT DOCUMENTS

| | | |
|---|---|---|
| JP | 54-16462 | 2/1979 |
| JP | 63-81243 | 5/1988 |
| JP | 4-15933 | 1/1992 |
| JP | 8-219968 | 8/1996 |
| JP | 8-254415 | 10/1996 |

OTHER PUBLICATIONS

H. Watanabe et al., "A New Stacked Capacitor Structure Using Hemispherical–Grain (HSG) Poly–Silicon Electrodes", 22$^{nd}$ Conference on Solid State Device and Materials, 1990, pp. 873–876.

* cited by examiner

Primary Examiner—Harshad Patel
(74) Attorney, Agent, or Firm—Sughrue Mion, PLLC

(57) ABSTRACT

Surface irregularity of a semiconductor device is measured with high accuracy, without being affected by the material properties of a semiconductor film forming the surface. Surface irregularity is evaluated when the semiconductor device is fabricated. This is accomplished using a plate-like element, which has a contact surface brought into contact with the surface of a test specimen. The plate-like element is then moved across the surface of the test specimen by a driving mechanism. The driving mechanism moves either the plate-like element or the test specimen relative to the other. A force caused by the motion is detected, and converted into a parameter equivalent to the friction coefficient between the test specimen and the contact surface. From the friction coefficient, surface irregularity is determined.

16 Claims, 12 Drawing Sheets

Fig.12 (a) (PRIOR ART)
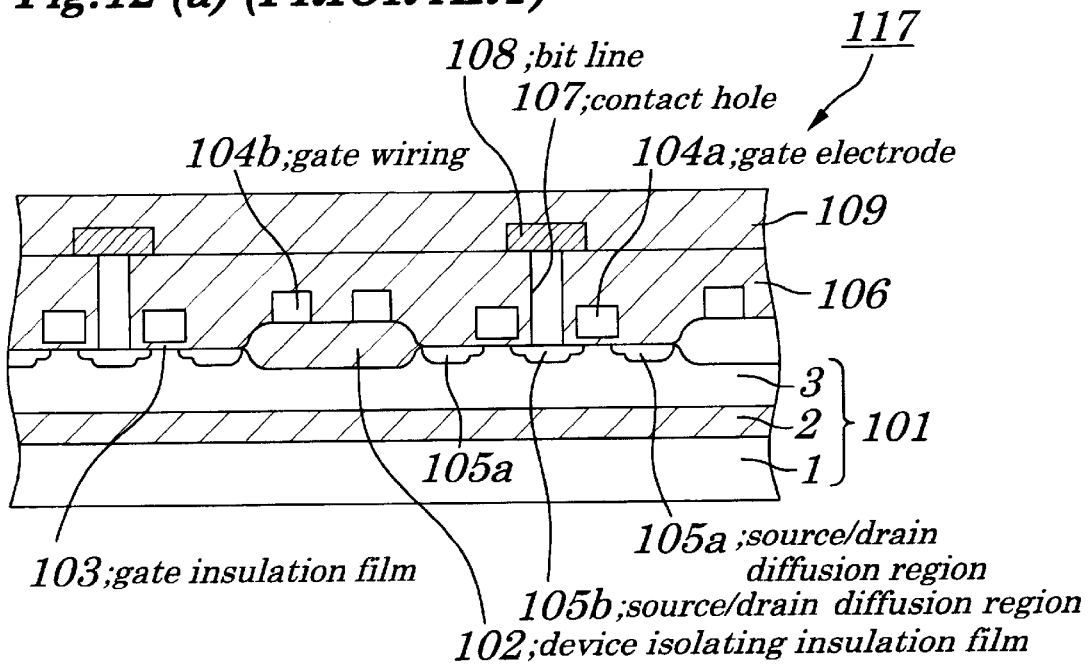
Fig.12 (b) (PRIOR ART)
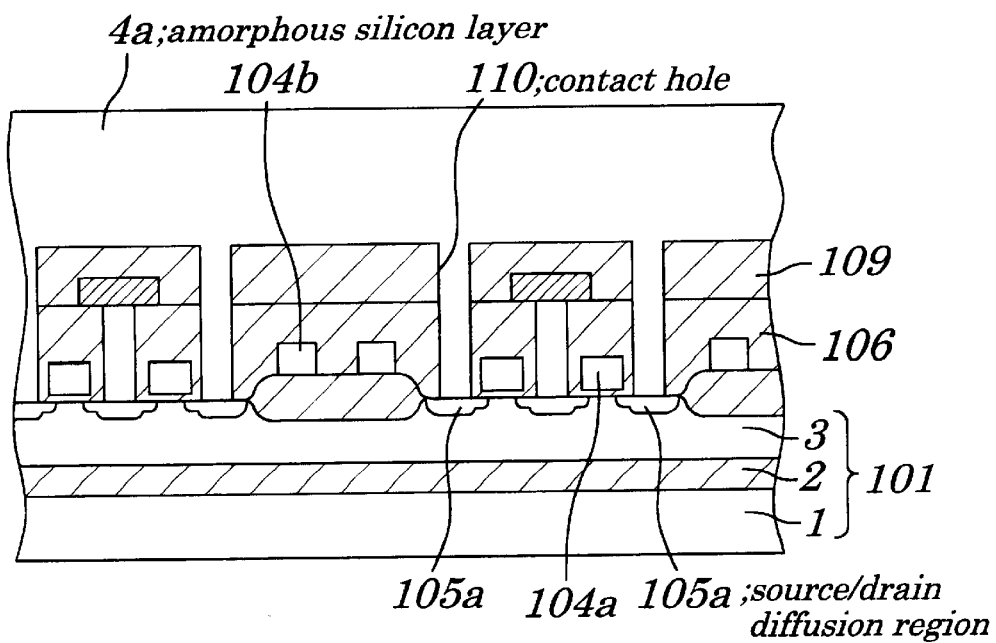

Fig.13 (a) (PRIOR ART)
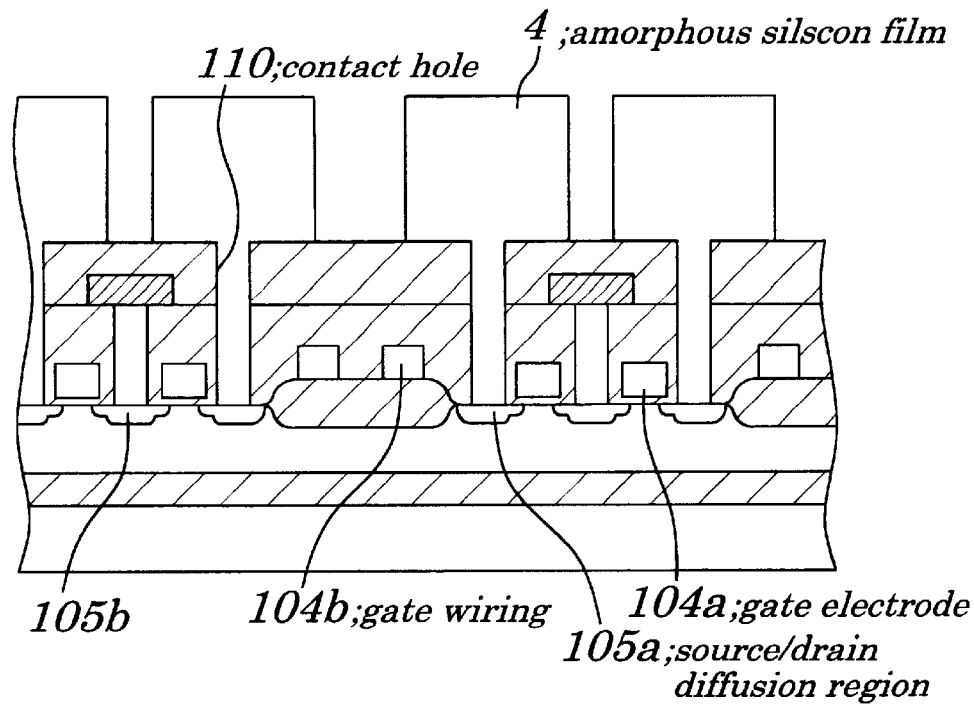
Fig.13 (b) (PRIOR ART)
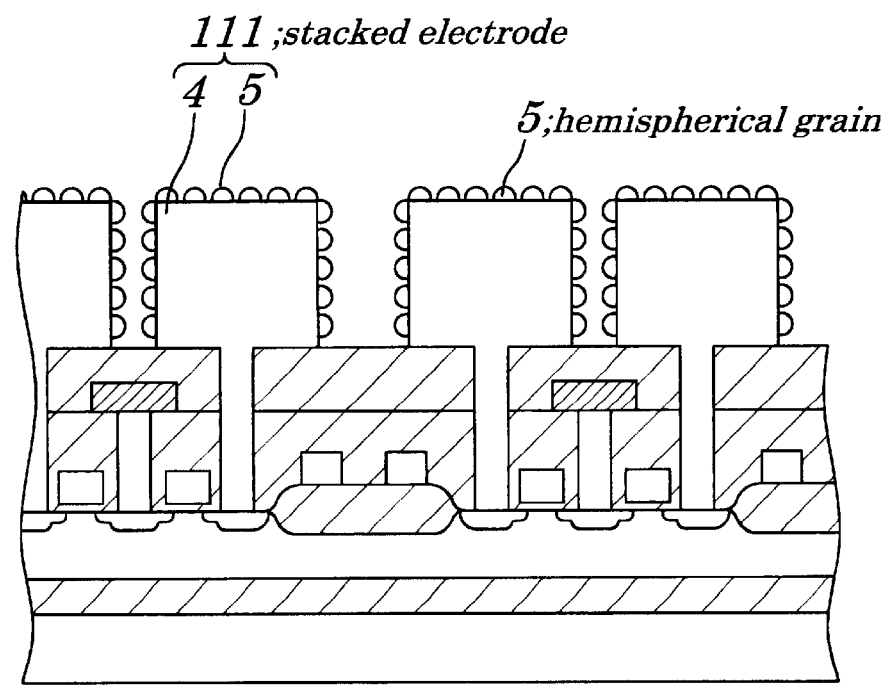

METHOD OF EVALUATING CAPACITANCE VALUE OF CAPACITOR ON SEMICONDUCTOR SUBSTRATE

BACKGROUND OF THE INVENTION

1. Field of the Invention

The present invention relates to an apparatus for and a method of evaluating surface irregularity, and more particularly to an apparatus for and a method of evaluating the surface irregularity, wherein the surface of an amorphous silicon film provided with hemispherical grains is monitored in degree of surface irregularity.

The present application claims the priority of Japanese Patent Application No. Heisei 10-037454 filed on Feb. 19, 1998, which is hereby incorporated by reference.

2. Description of the Related Art

In recent years, an integrated circuit of silicon semiconductors, particularly, DRAM (i.e., Dynamic Random Access Memory) shows in general a tendency to higher integration. As the higher integration of the semiconductor circuit reduces an effective area for forming a capacitor, various attempts have been made so as to increase an electrode area by modifying in structure the capacitor.

For example, H. Watanabe et. al have proposed a method for increasing a surface by forming hemispherical grains (i.e., HSG-Si: Hemispherical Grain Silicon) in a surface of an electrode, as disclosed in the following document: "A new stacked capacitor structure using hemispherical-grain polysilicon electrode", 22nd Conference on Solid State Device and Materials p. 873, 1990. A technique for forming the HSG-Si mentioned above is a technique for increasing a surface area by producing geometrical irregularity in a clean surface of a silicon layer through thermal, migration of silicon atoms to such surface.

FIG. 11 is a cross-sectional view of a DRAM, which includes a capacitor provided with a stacked electrode having the HSG-Si formed in its electrode surface. As shown in the same drawing, the DRAM is constructed of: an interlayer insulation film 109 of a device forming substrate 117, formed in which are an insulated-gate field effect transistor, a bit line 108 and a word line 104b; and, a capacitor 118, an interlayer insulation film 114, an aluminum wiring 115 and a cover insulation film 116 all of which are sequentially stacked together in the order of mention. The capacitor 118 is brought into contact with a source/drain diffusion region 105a through a contact hole 110 passing through both the interlayer insulation films 106, 109 of the device forming substrate 117. Incidentally, the device forming substrate 117 is constructed of: an SOI (Semiconductor On Insulator) substrate 101 in which a device forming semiconductor layer 3 is formed on a support substrate 1; a device separating insulation film 102 formed on the SOI substrate 101; a gate insulation film 103 and a gate electrode 104a both disposed above the device forming semiconductor layer 3; a gate (word) wiring 104b disposed, over the device separating insulation film 102; a pair of the source/drain diffusion regions 105a, 105b disposed in opposite sides of the gate electrode. 104a; the interlayer insulation film 106 covering these source/drain diffusion regions 105a, 105b; the bit line 108 brought into contact with the source/drain diffusion regions 105b through the contact hole 107 Of the interlayer insulation film 106; and, the interlayer insulation film 109 disposed on the bit line 108.

The capacitor 118 is constructed by sequentially stacking together a stacked electrode 111 of an amorphous silicon (a-Si) film 4, a capacitance insulation film 112 and a counter electrode (cell-plate electrode) 113 in the order of mention. Formed in the surface of the a-Si film 4 of the stacked electrode 111 are hemispherical grains 5.

In fabricating the capacitor 118 described above, at first, the device forming substrate 117 is produced.

Then, as shown in FIG. 12(b) the contact hole 110 is formed in the interlayer insulation films 106, 109 so as to reach an upper portion of the source/drain diffusion region. 105a. Subsequent to this, the a-Si film 4a which is brought into contact with the source/drain diffusion region 105a through the contact hole 110 is formed using a low pressure CVD process. After that, as shown in FIG., 13(a), the a-Si film 4a is subjected to a pattering process to assume the same shape as that of the stacked electrode 111. Then, the a-Si film 4 thus assuming the same shape as that of the stacked electrode 111 is heated under a reduced pressure, subjected to a $Si_2H_6$ gas in this condition, and then subjected to a nitrogen gas. Due to this, as shown in FIG. 13(b), the hemispherical grains 5 are formed in the surface of the a-Si film 4 so that the stacked electrode 111 is produced. Subsequent to this, both the capacitance insulation film 112 and the counter electrode 113 are formed on the stacked electrode 111 so that the capacitor 118 is produced. After that, through the conventional predetermined process steps, the DRAM as shown in FIG. 11 is produced.

In mass-producing the DRAM mentioned above, in order to reproduce a predetermined capacitance value of the capacitor 18, it is very important to evaluate the degree of irregularity of the surface of the a-Si film 4 immediately after the formation of the hemispherical grains 5 in the above surface.

Heretofore, as a method for evaluating the degree of irregularity of the surface, it has been known to measure the capacitance value of the capacitor actually produced by forming both the capacitance insulation film and the counter electrode on the stacked electrode 111 after the formation of the hemspherical grains 5. Further, it has been also known to monitor the irregularity of a surface of a test specimen through reduction in reflectance by measuring the reflectance of white light having been incident on the surface of the test specimen having the irregularity. In a further another conventional method, the degree of irregularity of the surface of the test specimen is evaluated through reduction in reflectance by measuring a secondary X ray with the use of a detector disposed in the side of reflection in a condition in which a monochromatic X ray is incident on the surface of the specimen at an angle of less than a critical angle, and, therefore totally reflected (see Japanese Patent Laid-Open Application No. Hei4-15933). In a still further another conventional method, as shown in FIG. 14(b), a light beam having a wavelength of less than 500 nm is incident on a surface of a test specimen, the surface being provided with irregularity. After that, as shown in FIG. 14(a), the light reflected from the above surface is measured in intensity to evaluate a capacitance value of a capacitor (see Japanese Patent Laid-Open Application No. Hei8-254415).

The conventional method, in which the degree of the irregularity of the surface of the test specimen is evaluated by measuring the capacitance value of the capacitor actually produced, is the most reliable method. However, in such conventional method, it is necessary to form the capacitance insulation film by deposition, and further necessary to form the counter electrode after the formation of the hemispherical grains (i.e., HSG-Si: Hemispherical Grain Silicon). Due to this, patterning of both the counter electrode and an extension for use in measurement is required, which causes the inconvenience of taking too much time and labor. Consequently, the conventional method is not very suitable for monitoring the surface irregularity in mass production.

On the other hand, another one of the conventional methods which uses the white light to measure the reflectance is simple, and, therefore suitable for monitoring the surface irregularity in mass production. However, when such conventional method is used as to the a-Si film, since the light used is visible light, the light passes through the silicon and is reflected at a boundary surface between the a-Si film and a film to produce, a reflected light. This reflected light varies intensity, depending on the optical properties of the material under the a-Si film. In addition to this, the light reflected at the boundary surface may interfere with light reflected at a surface of the a-Si film. Due to this, the reflectance is affected by both the thickness of the a-Si film and variations in optical constants. Due to this, a problem arises in that the conventional methods are poor in accuracy when used to monitor fine irregularity of the surface.

Further, there is another conventional monitoring method which uses the X-ray. In this method, problems arise in that its measuring spot can't be sufficiently reduced in diameter and that the X-ray radiates to a semiconductor device to excite electrons inside the device, which produces a new electron/hole pair it a channel portion of a transistor disposed under a capacitor, and, therefore impairs the performance of the device. Consequently, it is not adequate to apply this method to a process for manufacturing a product.

There is further another conventional monitoring method. In this method, light with a wavelength of equal to or less than 500 nm not capable of passing through a silicon layer is radiated to have its reflected light monitored. Since this method is not influenced by the thickness of the silicon layer and its substrate, this method is considered to be adequate in application. However, in measuring a test sample on which a pattern as shown in FIG. 14(b) is formed, in case that the pattern is too small in size relative to the radiation light, a transparent film having its portions partially disposed outside the pattern, and, therefore exposed them to the light produces interference components. Due to the presence of these interference components, as shown in FIG. 14(a), the reflected light is widely varies in intensity according to its wavelength. As a result, another problem arises in that this method is poor in measurement accuracy.

SUMMARY OF THE INVENTION

Under such circumstances, the present invention was made. Consequently, it is an object of the present invention to provide an apparatus for and a method of evaluating surface irregularity, which is not influenced by material of a specimen, is capable of obtaining a sufficient accuracy in measurement and further capable of preventing a semiconductor device and like elements from deteriorating in performance.

According to a first aspect of the present invention, the above object of the present invention is accomplished by providing an apparatus for evaluating a surface of a test specimen, comprising:
a plate-like element capable of moving in a condition in which it is brought into contact with the surface of the test specimen, the plate-like element being provided with a contact surface through which it is brought into contact with the surface of the test specimen;
a driving means for imparting a force for moving the test specimen or the plate-like element to the test specimen or to the plate-like element; and
a converter means for detecting a force received by the test specimen or by the plate-like element and for converting the force thus detected into a parameter such as a friction coefficient and like parameters equivalent to the friction coefficient.

According to a second aspect of the present invention, the converter means is constructed of a piezoelectric element fixedly mounted on the test specimen or on the plate-like element.

According to a third aspect of the present invention, the above object of the present invention is accomplished by providing:
a dropping-fluid means for dropping a fluid on the surface of the test specimen mounted on a specimen table;
a driving means for tilting the specimen table; and
a measurement means for measuring an inclination angle of the specimen table having been tilted.

According to a fourth aspect of the present invention, the driving means is constructed of a stepping motor; and
the measurement means for measuring the inclination angle of the specimen table is constructed of a means for detecting an angular position of the stepping motor.

According to a fifth aspect of the present invention, the above object of the present invention is accomplished by providing
a method of evaluating a surface of a test specimen, comprising:
evaluating in surface irregularity, particularly in size and in density, the surface of the test specimen by measuring a static friction coefficient or a kinetic friction coefficient in the surface of the test specimen.

According to a sixth aspect of the method of the present invention,
the surface of the test specimen is constructed of a semiconductor film which is provided with hemispherical grains in its surface.

According to a seventh aspect of the present invention,
a plate-like element is mounted on the surface of the test specimen, the plate-like element being provided with a contact surface;
in a condition in which the plate-like element has the contact surface brought into contact with the surface of the test specimen, the test specimen or the plate-like element is moved from rest, so that a force received by the test specimen or by the plate-like element is detected;
whereby a static friction coefficient or a kinetic friction coefficient in the surface of the test specimen is measured.

According to a further aspect of the present invention, fluid is dropped on the surface of the test specimen;
the test specimen is tilted to measure an inclination angle at which the fluid begins to flows;
whereby a static friction coefficient in the surface of the test specimen is evaluated.

According to a further aspect of the present invention, a surface area of an electrode of a capacitor formed on a semiconductor substrate or a capacitance value of the capacitor is evaluated by measuring the static friction coefficient or a kinetic friction coefficient in the surface of the test specimen.

According to a further aspect of the present invention,
a static friction coefficient or a kinetic friction coefficient in a surface of a conductive film or of an insulation film each formed on a semiconductor substrate is measured; whereby the surface of the conductive film or of the insulation film is evaluated in surface irregularity, particularly in size or in density.

BRIEF DESCRIPTION OF THE DRAWINGS

The above and other objects, advantages and features of the present invention will be more apparent from the following description taken in conjunction with the accompanying drawings in which:

FIGS. 12(a) and 12(b) show first cross-sectional views of the semiconductor in manufacturing the DRAM by the conventional method, illustrating the processing steps of the conventional method;

FIGS. 13(a) and 13(b) show second cross-sectional views of the semiconductor in manufacturing the DRAM by the conventional method, illustrating the processing steps of the conventional method;

Figure 14A:
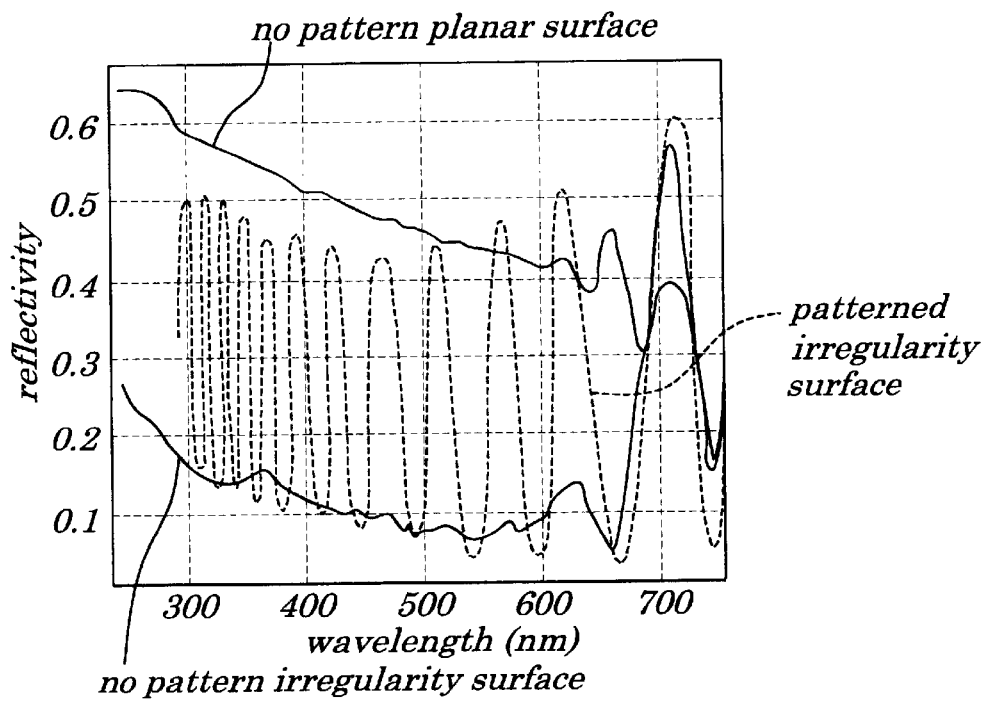
Figure 14B:
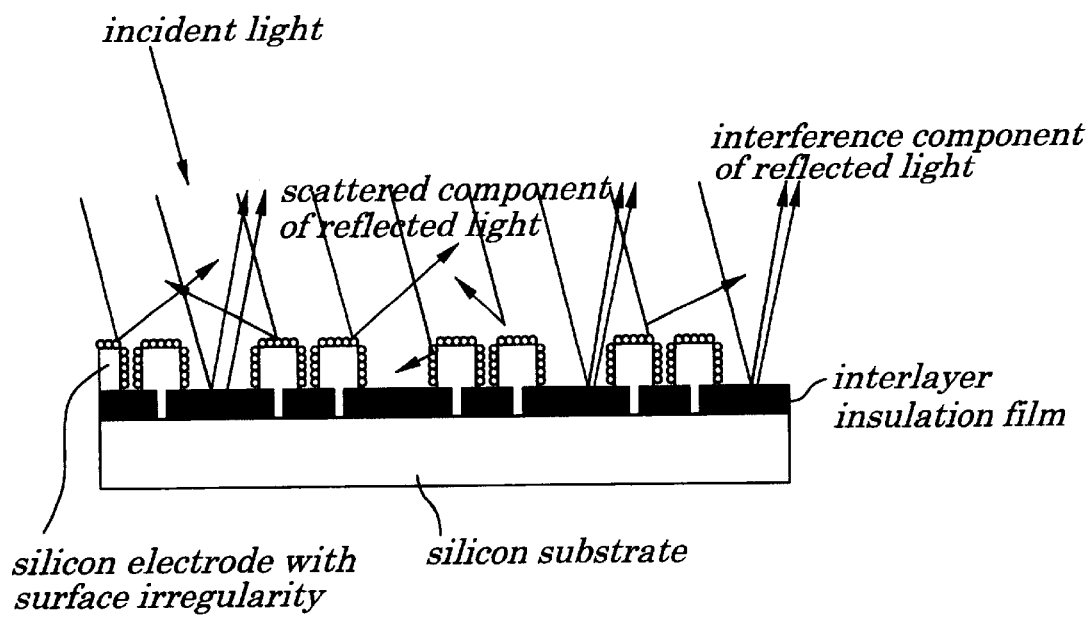

one of steps of a method of producing the vertical type MISFET;

FIG. 14(a) is a graph showing the results of measurement of the degree of the surface irregularity performed by the conventional method for evaluating the surface irregularity; and FIG. 14(b) is a cross-sectional view of the semiconductor, illustrating the processing steps of the conventional method.

DETAILED DESCRIPTION OF THE PREFERRED EMBODIMENTS

Figure 1:
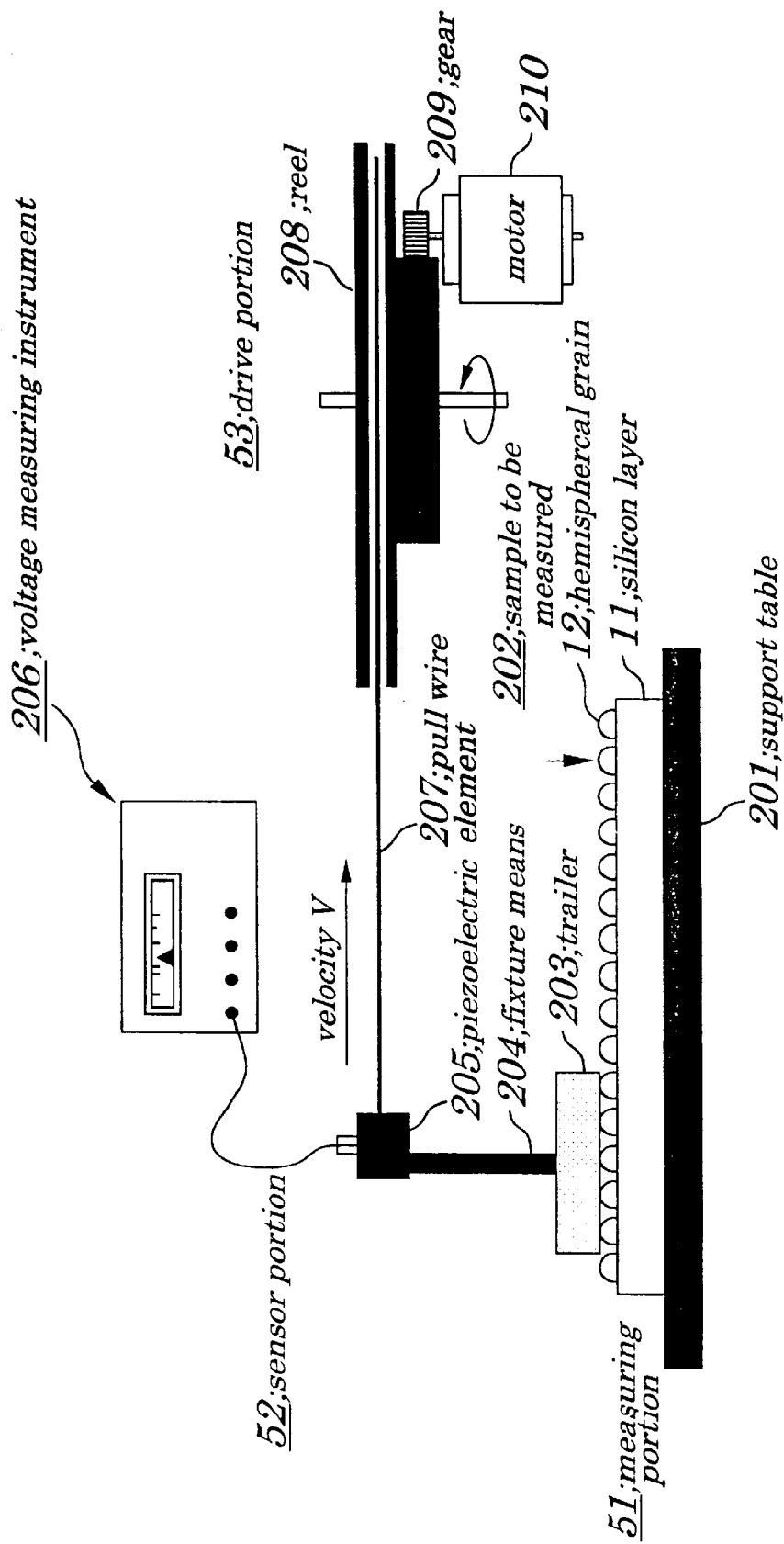
FIG. 1 is a schematic diagram of the apparatus for evaluating surface irregularity, which is used in the method of evaluating the surface irregularity according, to a first embodiment of the present invention.

Now, referring to the drawings, various preferred embodiments of the present invention will be described in detail.
Re: a First Embodiment of the Present Invention:

FIG. 1 shows a schematic diagram of an apparatus, i.e., measuring apparatus for evaluating surface irregularity, which is used in a method, i.e., monitoring method of evaluating the surface irregularity of an article, according to a first embodiment of the present invention.

The first embodiment of the present invention is based on the principle that it is possible to evaluate the surface irregularity of the test specimen in size and density on the basis of the degree of coefficient of friction. Namely, in general, the surface irregularity of the test sample has a tendency to decrease in size and density as the coefficient of static friction $\mu_0$ decreases. In other words, the surface irregularity of the test sample has a tendency to increase in size and density as the coefficient of static friction $\mu_0$ increases.

As shown in FIG. 1, the measuring apparatus of this first embodiment is constructed of a measuring portion 51, a sensor portion 52 and a drive portion 53.

The measuring portion 51 is constructed of: a support table 201 for supporting a sample to be measured (or evaluated); and, a trailer (i.e., plate-like element) 203, which is brought into contact with and moved along a surface of the sample. The trailer (i.e., plate-like element) 203 has at least a part of its surface bought into contact with the sample 202 and is made of quartz. The sensor portion 52 (which is means for detecting a force to which the plate-like element 203 is subjected, and for converting the thus detected force into a parameter identical in characteristics, with the coefficient of friction) is constructed of: a piezoelectric element 205 fixedly mounted on the trailer 203 through a fixture means 204; and, a voltage measuring instrument 206 provided with an amplifier and a voltmeter, the amplifier being connected with the piezoelectric element 205.

On the other hand, the driving portion (or means) 53 is constructed of: a pull wire 207 connected with the piezoelectric element 205; a reel 208 for taking up the wire 207; a gear 209 for transmitting rotational movement of a motor 210 to the reel 208; and, the motor 210 connected with the gear 209, for drive the trailer 203 through the piezoelectric element 205, pull wire 207, reel 208 and the gear 209.

In the measuring apparatus of the present invention having the above construction, when the trailer 203 is moved, the pull wire 207 connected with the piezoelectric element 205 is stretched to produce a tension (i.e., force for driving the plate-like element). Due to occurrence of such tension, the piezoelectric element 205 connected with the pull wire 207 generates a voltage (which is identical in characteristic with the coefficient of friction). This voltage is measured by the voltage measuring instrument 206.

Now, the principle of measurement in the measuring apparatus of the present invention will be described in detail.

First, the trailer 203 is put on the silicon layer 11 on the support table 201 in a manner such that the trailer 203 had its quartz surface brought into contact with the surface of the silicon layer 11. Then, the motor 210 of the drive portion 53 is energized to rotate, so that the trailer 203 is moved from rest to slide on the surface of the silicon layer 11 at a predetermined value of the velocity v.

At this time, in order to move the trailer 203 from rest, a force $F_0$, which is given by the following equation (1) and corresponds to the static friction coefficient $\mu_0$ of a surface being measured, is required:

$$F_0 = \mu_0 \cdot N \tag{1}$$

Where: N is a normal force (m·g)
m is the mass of the trailer; and
g is a gravitational acceleration.

This force $F_0$ is generated by the motor 210, and transmitted to the pull wire 207. Due to this, a voltage proportional to the force $F_0$ is generated in the piezoelectric element 205 connected with the pull wire 207.

Further, as shown in the following equation (2), after start of the trailer 203, in order to keep a constant value of the velocity v, it is necessary to continuously pull the trailer 203 with a force F corresponding to the kinetic friction coefficient $\mu$ of the surface being measured. The force F required to keep the constant velocity v of the trailer 203 varies in accordance with the kinetic friction coefficient $\mu$, as follows:

$$F = \mu \cdot N \tag{2}$$

Consequently, the piezoelectric element 205 may generate a voltage proportional to the force F. The voltage thus generated is amplified by the amplifier of the voltage measuring instrument 206 connected with the piezoelectric element. The thus amplified voltage is measured by the voltmeter.

Eventually, based on the thus measured voltage, both the static friction coefficients $\mu_0$ and the kinetic friction coefficient $\mu$ are calculated. Since the degree of each of the static friction coefficient $\mu_0$ and the kinetic friction coefficient $\mu$ varies on the basis of the degree of the surface irregularity of the silicon layer 11, it is possible to evaluate the degree of the surface irregularity of the silicon layer 11 on the basis of a value of each of the static friction coefficient $\mu_0$ and the kinetic friction coefficient $\mu$ by previously finding out the relationship between the degree of the surface irregularity and each of the static friction coefficient $\mu_0$ and the kinetic friction coefficient $\mu$.

Figure 2:
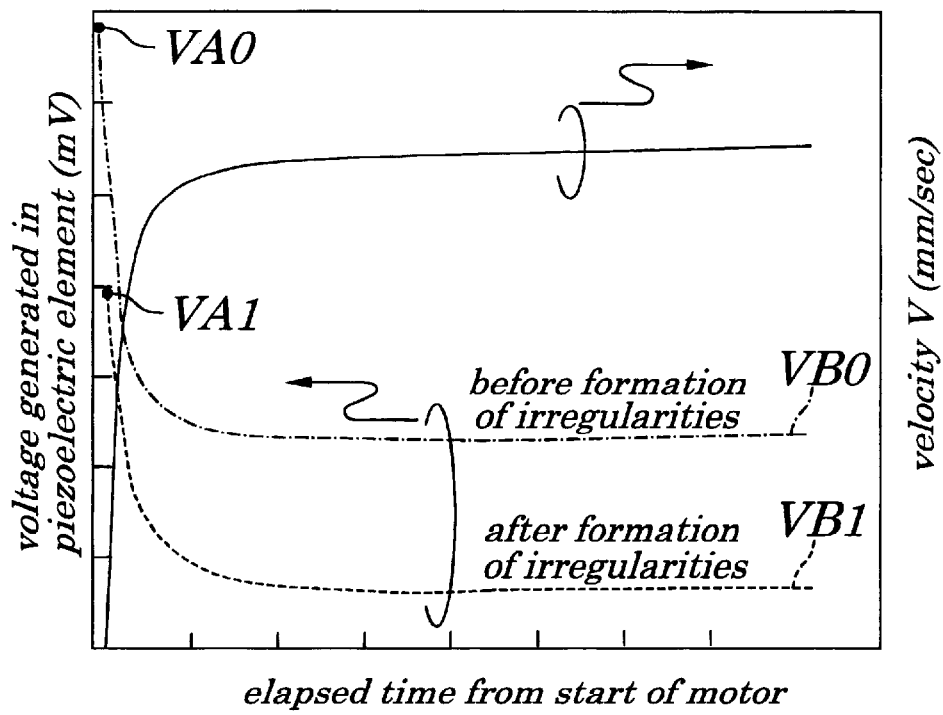
FIG. 2 is a graphic illustration of the relationship between the degree of surface irregularity and the voltage generated in the piezoelectric element, obtained by the method of the present invention according to the above first embodiment, wherein the voltage corresponds to the frictional coefficient of the surface.

FIG. 2 is a characteristic diagram showing the measurement results of voltage generated by the piezoelectric element when the trailer 203 slides on the surface of the silicon layer 11 in a condition in which the hemispherical grains are formed in the surface of the silicon layer 11. In this diagram, a y-axis shows in linear scale both the generated voltage (mV) of the piezoelectric element 205 and the velocity v (mm/sec) of the trailer 203, while an x-axis shows in linear scale the elapsed time (any time unit) after start of the motor 210. The voltages are measured by the use of the measuring apparatus shown in FIG. 1. In measuring the voltages the motor 201 is controlled in rotational speed in a manner such that the trailer 203 moves at a constant velocity.

Further, in FIG. 2, generated voltage VA0 and VA1 of the piezoelectric element 205 correspond to those of the static friction coefficient $\mu_0$ before and after formation of the hemispherical grains, respectively. On the other hand, the other generated voltages VB0 and VB1 appearing in a range where the velocity v of the trailer 203 reaches a predetermined value correspond to those of the kinetic friction coefficient $\mu$ before and after formation of the hemispherical grains, respectively. Incidentally, any of these friction coefficients are proportional to a voltage generated in the piezoelectric element 205. As is clear from FIG. 2, once the hemispherical grains are formed, the thus formed hemispherical grains reduce the generated voltage of the piezoelectric element 205, and reduce the friction coefficient. Both the static and the kinetic friction coefficient show the same tendency. Incidentally, FIG. 2 shows the measurement results in a condition in which the silicon layer 11 provided with the hemispherical grains is sufficiently larger in area than the contact surface of the trailer 203.

In contrast with this, when the surface of the silicon layer 11 provided with the hemispherical grains is smaller in area than the contact surface of the trailer 203 and an immense number of the small-area silicon layers 11 become united to form a surface, it is necessary for the measuring apparatus to compensate for a difference in the generated voltages due to a difference in pattern area. For example, in case that the trailer 203 with a contact area of 1000 $\mu$m×2000 $\mu$m is used and that an immense number of patterns each with an area of approximately 1 $\mu$m×1 $\mu$m are widely disposed, it is possible to compensate for a difference in the generated voltages by using, as a coefficient, an area ratio of the entire surface area to a total area of all the patterns.

Figure 3:
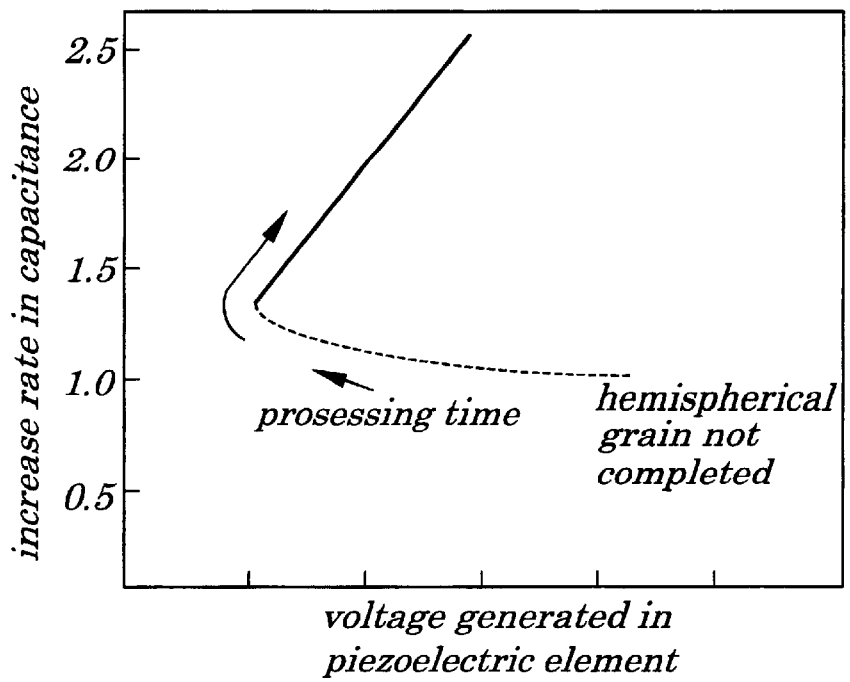
FIG. 3 is a graphic illustration of the relationship between the increment rate in capacitance of the capacitor and the voltage generated in the piezoelectric element in the surface of the stacked electrode, obtained by the method of the present invention according to the first embodiment.

FIG. 3 is a graph showing the relationship between the capacitance of the capacitor and the generated voltage of the piezoelectric element 205 when the hemispherical grains vary in density due to variations in exposure period of time in an $Si_2H_6$ gaseous atmosphere. The generated voltage of the piezoelectric element 205 corresponds to the kinetic friction coefficient $\mu$. In the graph shown in FIG. 3, a y-axis shows in linear scale an increase rate in capacitance of the capacitor, while an x-axis shows in linear scale the generated voltage of the piezoelectric element 205. The increase rate of capacitance is determined on the basis of a capacitance obtained at a time when the capacitance insulation film is formed on a flat surface of a stacked electrode.

As is clear from FIG. 3., immediately after exposure to the $Si_2H_6$ gaseous atmosphere, the generated voltage of the piezoelectric element 205 shows a large value. This is probably because the hemispherical grains are not formed so that the friction remains at a large value. Further exposure to the $Si_2H_6$ gaseous atmosphere causes the generated voltage of the piezoelectric element 205 to rapidly decrease. In other words, this is probably because the hemispherical grains are formed to reduce the friction. In contrast with this, still further exposure to the $Si_2H_6$ gaseous atmosphere causes the generated voltage of the piezoelectric element 205 to increase. This is probably because of the hemispherical grains increase to cause the friction to increase.

At this time, a surface area "A" of the silicon layer 11 increases in proportional to the size and the density of the hemispherical grains. As for the capacitance C, as shown in the following equation (3), it is proportional to the above surface area "A":

$$C = \epsilon_0 \cdot \epsilon \cdot A / t \tag{3}$$

Where: t is a film thickness of the capacitance insulation film;

$\epsilon_0$ is a dielectric constant of a vacuum; and $\epsilon$ is a relative dielectric constant of the capacitance insulation film.

Further, the kinetic friction coefficient is also proportional to both the size and the density of the hemispherical grains. Due to this, a proportional relationship between the capacitance and the generated voltage of the piezoelectric element 205 is obtained.

Namely, in a condition in which the hemispherical grains are formed and the relationship between the capacitance and the generated voltage of the piezoelectric element 205 is previously known, it is possible to indirectly measure the capacitance C by measuring the generated voltage of the piezoelectric element 205 without directly measuring the capacitance C, so long as the same pattern is used.

Further, if necessary, based on the capacitance C, it is possible to calculate the surface area "A" of the silicon layer 11 by using the following equation (4):

$$A = C \cdot t / (\epsilon_0 \cdot \epsilon) \qquad (4)$$

As described above., in this embodiment, only by moving the trailer 203 on the surface of the test specimen to measure the generated voltage of the piezoelectric element 205, it is possible to evaluate both the capacitance C and the surface area "A" of the silicon layer 11 in an easy manner.

Further, since no light is used in the above, there is no error derived from reflection. Due to this, it is possible to carry out precise measurement, which is free from any influence of a material being measured, i.e., of the test specimen.

Incidentally, since the test specimen has its surface brought into physical contact with the trailer 203, there is a fear that the surface of the test specimen is physically damaged. However, this fear can be avoided using the trailer 203 with a moderate weight, which is moved at a moderate velocity v.

Referring now to FIGS. 4(a) to 7, there is shown a method for fabricating a DRAM using the method of evaluation of this embodiment, which will be described.

Figure 7:
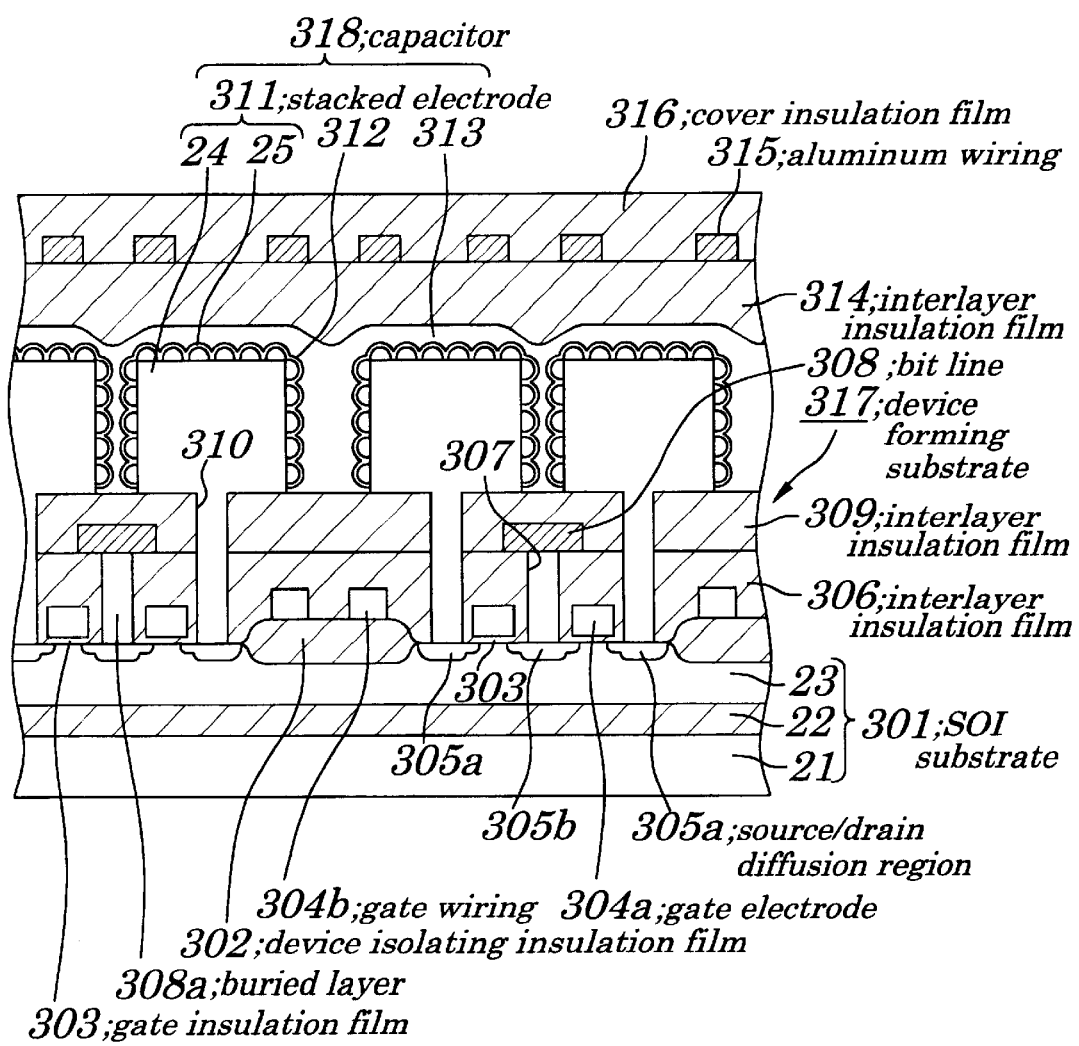
FIG. 7 shows a fourth cross-sectional view of the semiconductor in manufacturing the DRAM by the method of the present invention according to the first embodiment, illustrating the processing steps of the method of the present invention.

First, the DRAM will be described in construction. As shown in FIG. 7, in the DRAM, formed in the following order of mention on the interlayer insulation film 309 of the device forming substrate 317 provided with the insulation gate field effect transistor, bit line 308, word line 304b and like components are: the capacitor 318; the interlayer insulation film 314; the aluminum wiring 315; and, the cover insulation film 316. The capacitor 318 has its stacked electrode 311 brought into contact with the source/drain diffusion region 305a through the contact hole 310, which is formed in the interlayer insulation films 306, 309.

The device forming substrate 317 is constructed of: an SOI substrate 301, comprising a support substrate 21, an insulation layer 22, and a device forming semiconductor layer. 23; a device isolating insulation film 302 disposed on the SOI substrate 301; a gate insulation film 303 and a gate electrode 304a both disposed on the device forming substrate 23 between the device isolating insulation films 302; a gate wiring (i.e., word line) 304b disposed on the device isolating insulation film 302; source/drain diffusion regions 305a, 305b disposed on the surfaces of the device forming semiconductor layers 23 disposed in opposite sides of the gate electrode 304a; an interlayer insulation film 306 covering both the gate electrode 304a and the gate wiring 304b; the bit line 308 connected with the source/drain diffusion region 305b through a contact hole 307 of the interlayer insulation film 306; and, the interlayer insulation film 309 disposed on the bit line 308.

The capacitor 318 of the above DRAM is constructed by stacking the following components in the order of mention: namely, the stacked electrode 311 formed of an amorphous-Si film (hereinafter referred to as the a-Si film) 4; a capacitance insulation film 312 formed of both an $Si_3N_4$ film and an $SiO_2$ film; and, a counter electrode (i.e., cell plate electrode) 313. Formed on a surface of the a-Si film 24 of the stacked electrode 311 are the hemispherical grains 25.

In fabricating the DRAM having the above construction, first, as shown in FIG. 4(a), after a device isolating insulation film 22 formed of a silicon oxide film on a device forming semiconductor layer 21 is formed, the gate insulation film 303 is formed on the device forming semiconductor layer 21. Formed on this gate insulation film 303 is the gate electrode 304a. Then, an ion implantation process is carried out to form the source/drain diffusion regions 305a, 305b each with a high concentration of an impurity in the device forming semiconductor layer 21 disposed in the opposite sides of the gate electrode 304a. After that, by using a CVD (i.e., Chemical Vapor Deposition) process, the contact hole 307 for connecting the source/drain region 305b to the interlayer insulation film 306 on this source/drain region 305 is formed. Then, by using the CVD process, the a-Si film with a phosphorus concentration of $3 \times 10^{20}$ atoms/cm$^3$ is deposited. Thereafter, the entire surface is etched by the dry etching process. As a result, the contact hole 307 is filled with the a-Si film to form a buried layer 308a.

Then, by using an RF sputtering process, a tungsten silicide film with a film thickness of approximately 100 nm is deposited. Subsequent to this, by using both the photolithography process and the dry etching process, patterning of the tungsten silicide film is carried out to form the bit line 308 brought into contact with the buried layer 308a. Then, by using the CVD process, the interlayer insulation film 309 is formed. Through the above processes, the device forming substrate 317 is formed.

Next, as shown in FIG. 4(b), by using both, the photolithography process and the dry etching process, patterning of the interlayer insulation films 309, 306 is carried out to form the contact hole 10 which reaches down to the source/drain diffusion region 305a of the transistor. Subsequently, by using the CVD process, another one 24a of the a-Si film with a phosphorus concentration of $3 \times 10^{20}$ atoms/cm$^3$ is formed on the interlayer insulation film 309. This a-Si film 24a is filled also in the contact hole 310. Then, as shown in FIG. 5(a), by using both the photolithography technique and the dry etching technique, patterning of the a-Si film 24a is carried out to form a stacked electrode. The a-Si film 24 assuming a shape of the stacked electrode is brought into contact with the source/drain diffusion region 305a through the contact hole 310.

After that, by using the following process, the hemispherical grains are formed in the surface of the a-Si film 24. In other words, first, the a-Si film 4 has its surface exposed to a liquid mixture prepared in the proportions of 1 part HF and 100 parts water (i.e., HF:$H_2O$=1:100), so that, when a natural oxide film exists in the surface of the a-Si film 24, such natural oxide film is removed.

Subsequently, the a-Si film 24 is exposed to the $Si_2H_6$ gaseous atmosphere for 3 minutes at a pressure of 1 mTorr. Due to this, fine seed crystals are formed in the surface of the a-Si film 24. Then, in a condition in which a temperature of 570° C. is kept, an annealing treatment is applied for 10 minutes in an atmosphere of nitrogen, which causes silicon atoms to move through migration so as to gather around each of the seed crystals, whereby the hemispherical grains (i.e., irregularity) 25 are formed.

After that, the trailer 203 of the measuring apparatus shown in FIG. 1 is brought into contact with the surface of the device forming substrate 317 provided with the a-Si film 24 having the hemispherical grains 25, and is then moved to measure the generated voltage of the piezoelectric element 205. Subsequently, as described above, by using the graph of FIG. 3, both the capacitance C and the surface area "A" of the silicon layer 11 are evaluated on the basis of such generated voltage of the piezoelectric element 205. When the capacitance C and the surfaced area "A" of the silicon layer 11 are within a desired range, it is judged that the stacked electrode 311 is completed. Then, the subsequent step is carried out.

Now, in an atmosphere of ammonia (i.e., $NH_3$), at a temperature of 1000° C., a heating treatment is carried out for 1 minute to realize thermal nitriding of the surface of the a-Si film 24 having the hemispherical grains 25. Further, by the CVD process using $NH_3$ and $SiH_2Cl_2$, an $Si_3N_4$ film is formed.

Then, in an atmosphere of hydrogen and oxygen, at a temperature of approximately 900° C., a thermal oxidation treatment is applied to form an $SiO_2$ film on the $Si_3N_4$ film. As a result, as shown in FIG. 6(a), the capacitance insulation film 312 constructed of both the $Si_3N_4$ film and the $SiO_2$ film is formed. Subsequent to this as shown in FIG. 6(a), by using the CVD process, the a-Si film with a phosphorus concentration of $3 \times 10^{20}$ atoms/$cm^3$ is formed on the capacitance insulation film 312. The thus formed a-Si film forms a cell plate electrode 313. Through the above processes, the capacitor 318 constructed of the stacked electrode 311, capacitance insulation film 312, and the cell plate electrode 313 is formed.

Then, by using the CVD process, a BPSG film forming the interlayer insulation film 314 is formed. Subsequent to this, by using the RF process, an aluminum film is formed on the interlayer insulation film 314. After that, by using both the photolithography technique and the dry etching technique, the aluminum wiring 315 is formed.

Then, by using the plasma CVD process, an $SiO_2$ film forming the cover insulation film 316 is formed. Due to this, as shown in FIG. 7, the DRAM having the capacitor 318 with, a desired capacitance is completed.

As described above, according to the method for fabricating the DRAM of this embodiment, it is possible to evaluate in an easy manner both the capacitance C and the surface area "A" of the stacked electrode 311 through measurement with a sufficient accuracy, while the measurement is not influenced by a material being applied. Further, since there is not used any light and any liquid chemicals, the surface of the test specimen is free from any chemical deterioration. Due to this, it is possible to prevent the transistors such as the DRAMs and the like from deteriorating in properties. Consequently, when this method of evaluation is applied to the mass production of the DRAMs, it is possible to mass-produce the DRAMs which are uniform in properties and quality with each other. In each of the DRAMs thus mass-produced, the capacitor 318 with a predetermined capacitance value can be reproduced.

Regarding a Second Embodiment of the Present Invention

Now, with reference to FIGS. 8 to 10(a), the second embodiment of the present invention will be described.

In this second embodiment, a fluid or test liquid is dropped at the surface of the test specimen to use the relationship between: the degree of an inclination angle in surface of the test specimen at a time when the thus dropped test liquid begins to flow on the above surface; and, the degree of the static friction coefficient $\mu_0$.

More particularly, by keeping constant in mass (or, weight) the test liquid resting on the surface of the test specimen, it is possible to have a tangent of the inclination angle $\theta_c$ of the test specimen relative to a horizontal plane be proportional to the static friction coefficient $\mu_0$, as shown in the following equation (5):

$$F = \mu_0 \cdot \text{Nliq} \qquad (5)$$

Where: Nliq is a normal force (=mliq·g );

g is a gravitational acceleration;

$\mu_0$ is a static friction coefficient (=$\tan\theta_c$); and $\theta_c$ is an inclination angle in surface of the test specimen relative to a horizontal plane at a time when the test liquid on the surface begins to flow.

In this second embodiment of the present invention, since the test liquid is used, it is difficult to find out a value of the static friction coefficient. Due to this, the degree of irregularity in surface (hereinafter referred to as the surface irregularity) of the test specimen is relatively or absolutely evaluated in connection with the degree of the inclination angle $\theta_c$ in surface of the test specimen. However, in absolutely evaluating the surface irregularity, it is necessary to previously find out the relationship between: the inclination angle in surface of the test specimen; and, the degree of the surface irregularity, and evaluate the surface irregularity under the same conditions as used in finding out the above relationship.

Figure 8:
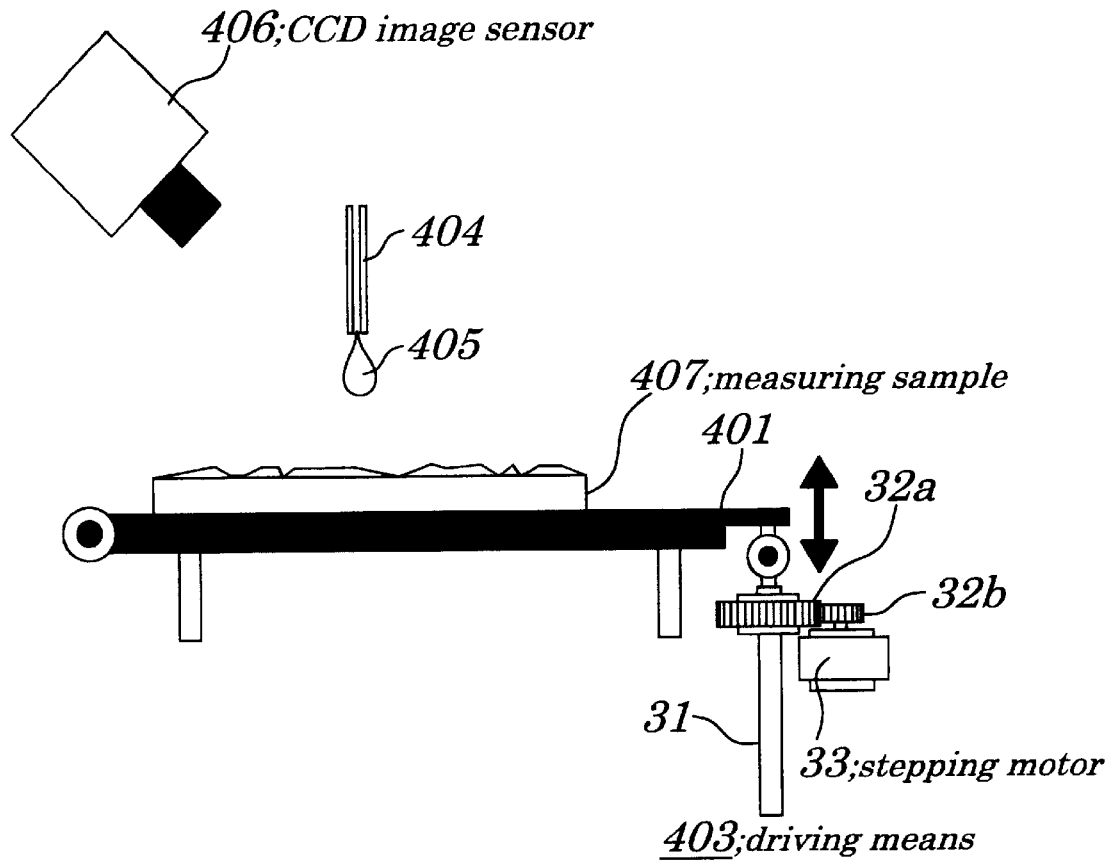
FIG. 8 is a schematic diagram of the apparatus for evaluating surface irregularity, which is used in the method of evaluating the surface irregularity according to a second embodiment of the present invention.

FIG. 8 is a schematic diagram showing in construction the measuring apparatus of this embodiment used in the method for evaluating a surface of metal. As shown in this drawing, the measuring apparatus is substantially constructed of: a sample table 401 on which a measuring sample (i.e., sample to be measured) 407 is fixedly mounted; a driving means 403 constructed of a stepping motor 33, gears 32a and 32b, and a screw 31 moved up and down through rotational movement of the gear 32a; a nozzle (for dropping a fluid or test liquid) 404; and, a CCD (i.e., Charge Coupled Device) image sensor 406.

Now, a method for monitoring the surface of metal through the measuring apparatus having the above construction will be described.

First, the measuring sample 407, on which a metal film with a surface irregularity is formed, is put on the sample table 401. Next, as the test liquid 405, mercury is dropped off from the nozzle 404 to the metal film with the surface irregularity in a manner such that a mass of the test liquid 405 thus dropped is always kept at the same value. After that, the CCD image sensor 406 monitors the location of the test liquid 405 on the surface of the metal film. Then, the stepping motor 33 is energized to rotate so that the sample table 401 has one of its opposite sides moved up or down, where by the sample table is gradually inclined. When the sample table 401 reaches a predetermined value of the inclination angle $\theta_c$, the test liquid 405 begins to flow on the metal film.

Such predetermined value of the inclination angle $\theta_c$ is determined on the basis of a rotation angle of the stepping motor 33. After that, based on this value of the inclination angle $\theta_c$, the surface irregularity is evaluated.

Figure 9:
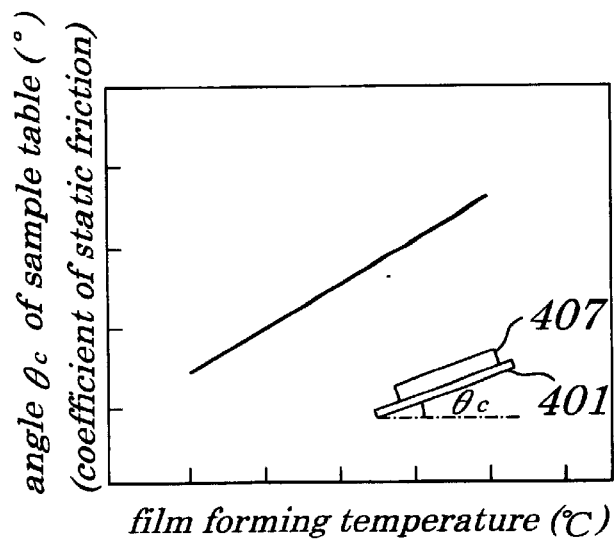
FIG. 9 is a graph showing the relationship between: the tilting angle of the test sample table at a time when a fluid begins to flow, corresponding the degree of the irregularity of the surface of the aluminum film; and, the temperature at which the aluminum film is formed, the graph being obtained by the method of the present invention according to the above second embodiment.

FIG. 9 is a graph showing an example in which the correlation between: a substrate temperature at a time when the aluminum film is formed; and, the value of the inclination angle $\theta_c$ (or, static friction coefficient) of the sample table 401 is known. In this graph, a y-axis shows in linear scale the inclination angle $\theta_c$ (·) of the sample table 401, while an x-axis shows in linear scale the film-forming temperature (° C.).

By using the RF (i.e., Radio Frequency) sputtering process, the aluminum film is formed at a temperature varying from 100 to 400° C. At this time, as the test liquid 405, mercury is used. As is clear from FIG. 9, as the substrate temperature at a time when the film is formed increases, the surface irregularity of the aluminum film increases in size. It has been found that the surface irregularity of the aluminum film reaches its minimum size at the substrate temperature of 100° C., at which the inclination angle $\theta_c$ or the static friction coefficient $\mu_0$ reaches its minimum value within a range of the substrate temperature having been experimented. As a result, it has been found that the aluminum film with small-size surface irregularity is formed at a temperature of 100° C.

Figure 4:
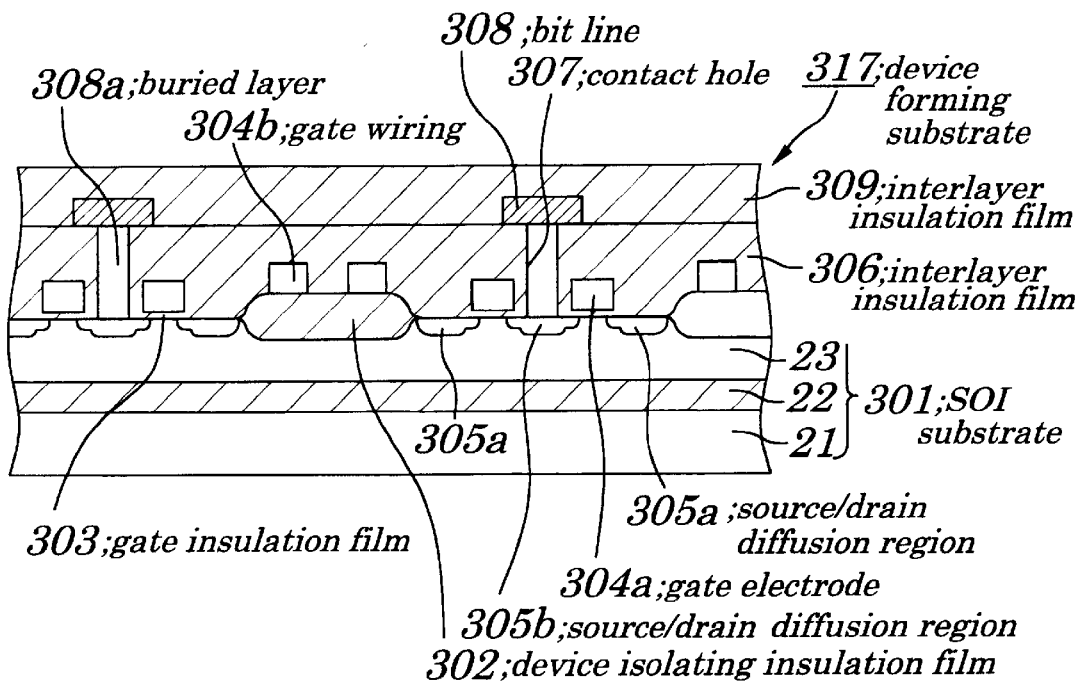
FIGS. 4(a) and 4(b) show first cross-sectional views of the semiconductor in manufacturing the DRAM by the method of the present invention according to the first embodiment, illustrating the processing steps of the method of the present invention.
Figure 4:
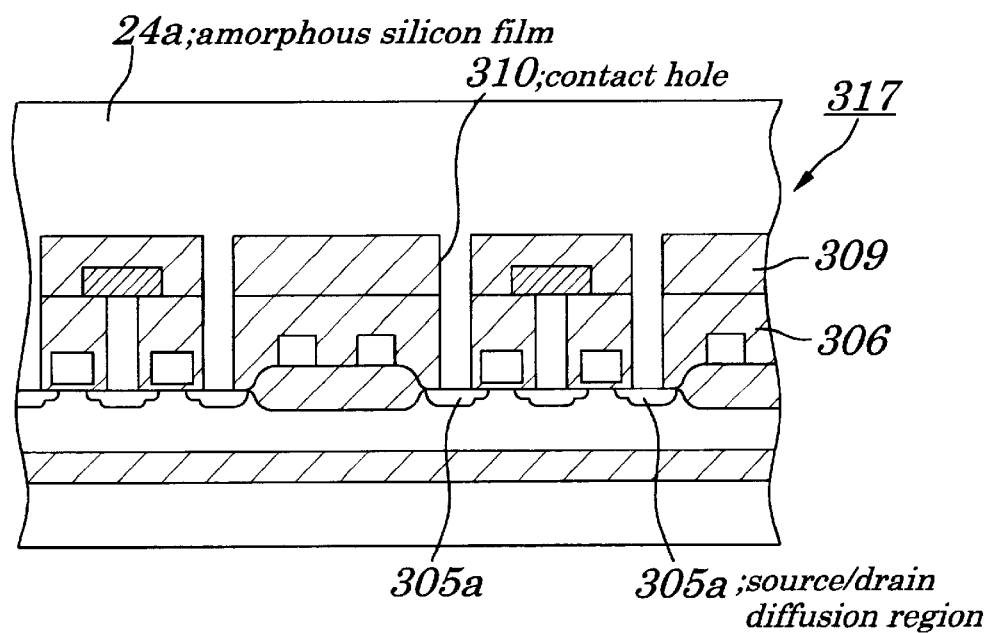
Figure 5:
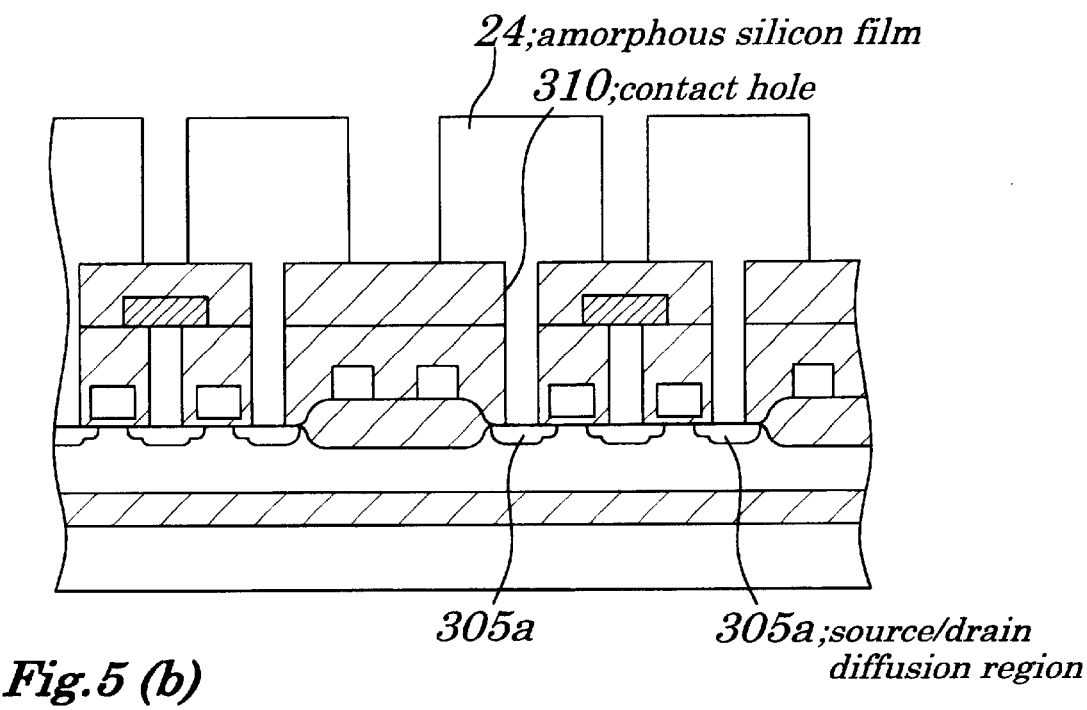
FIGS. 5(a) and 5(b) show second cross-sectional views of the semiconductor in manufacturing the DRAM by the method of the present invention according to the first embodiment, illustrating the processing steps of the method of the present invention.
Figure 5:
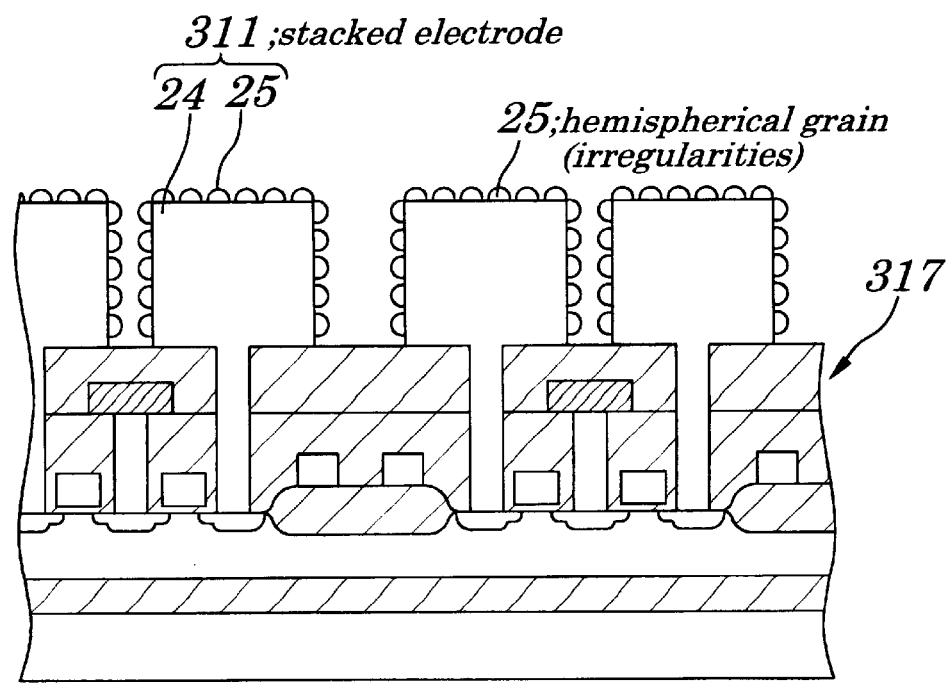
Figure 6:
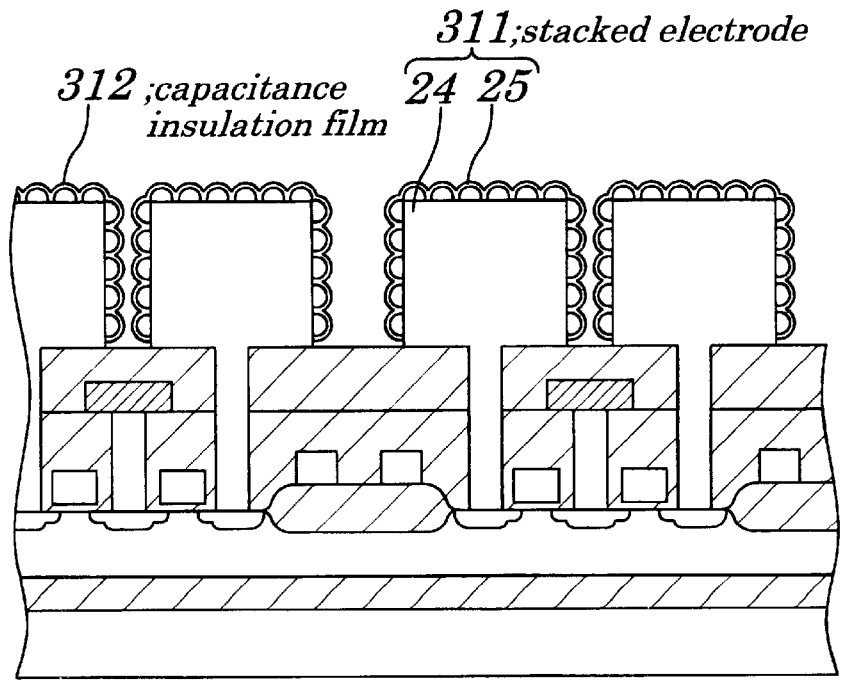
FIGS. 6(a) and 6(b) show third cross-sectional views of the semiconductor in manufacturing the DRAM by the method of the present invention according to the first embodiment, illustrating the processing steps of the method of the present invention.
Figure 6:
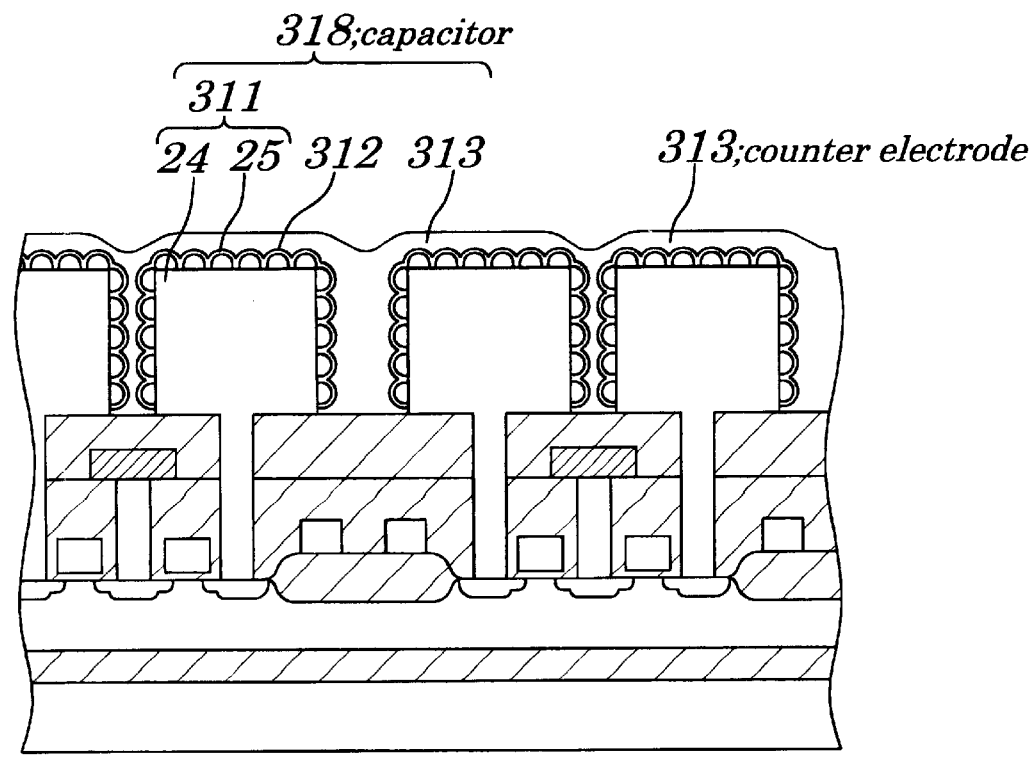

Now, with reference to FIGS. 4(*a*) to 10(*b*), the method for fabricating the DRAMs using the method of evaluation of this embodiment will be described. First, by using the RF sputtering process, the substrate temperature is varied to form the aluminum film, so that the correlation between: a value of the substrate temperature at a time when the aluminum film is formed; and, a value of the inclination angle $\theta_c$ of the sample table 401 at a time when the test liquid 405 begins to flow on the surface of the aluminum film is previously obtained. When the substrate temperature is varied within a range of, for example, from 100 to 400° C., the graph of FIG. 9 is obtained. Preferably, the substrate temperature is varied in its range according to the type of a film being measured. Further, it is necessary to select the test liquid 405 of a type having hydrophobic properties relative to the surface of the test specimen. In other words, the test liquid thus selected does not wet the surface of the test specimen, and is good in fluidity. Then, the same process steps as those (shown in from FIG. 4(*b*) to FIG. 6(*b*)) are carried out. Thereafter, the interlayer insulation film 314 is formed on the cell plate electrode 313.

Figure 10:
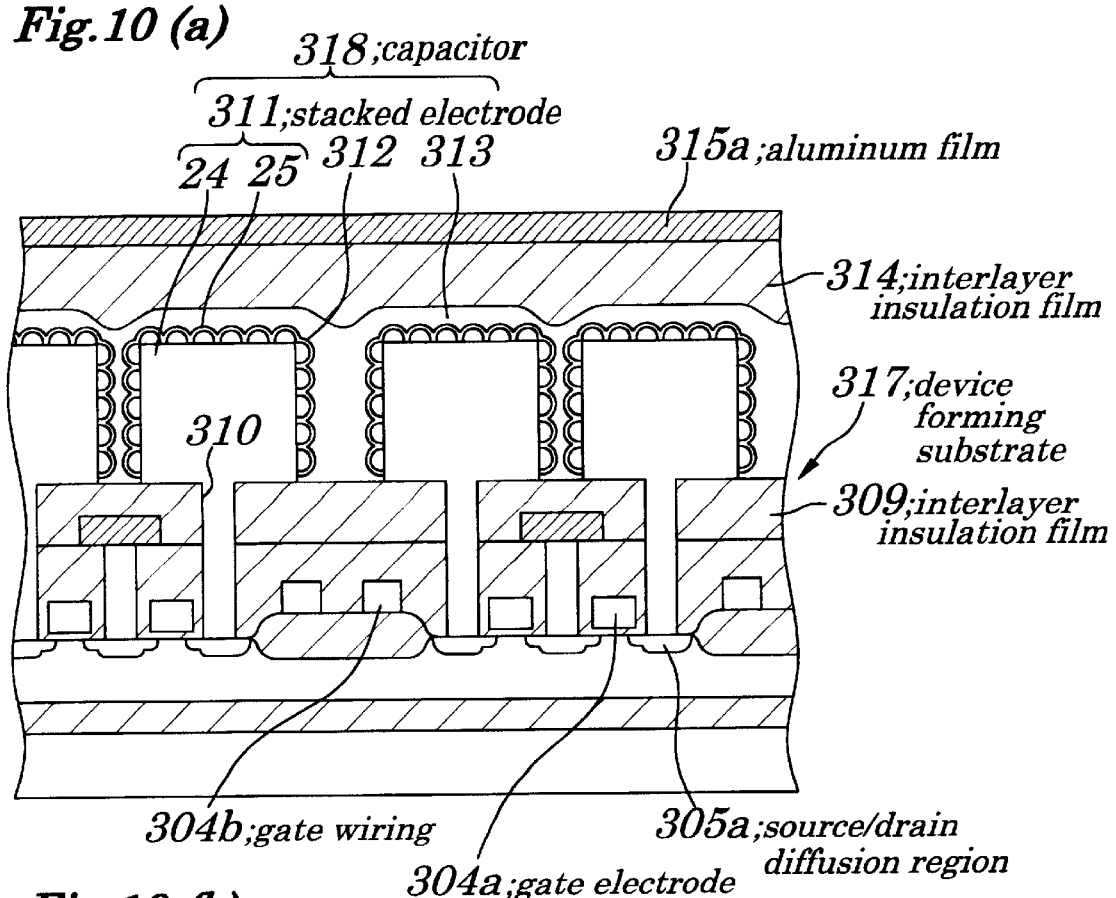
FIGS. 10(a) and 10(b) show cross-sectional views of the semiconductor in manufacturing the DRAM by the method of the present invention according to the second embodiment, illustrating the processing steps of the method of the present invention.
Figure 10:
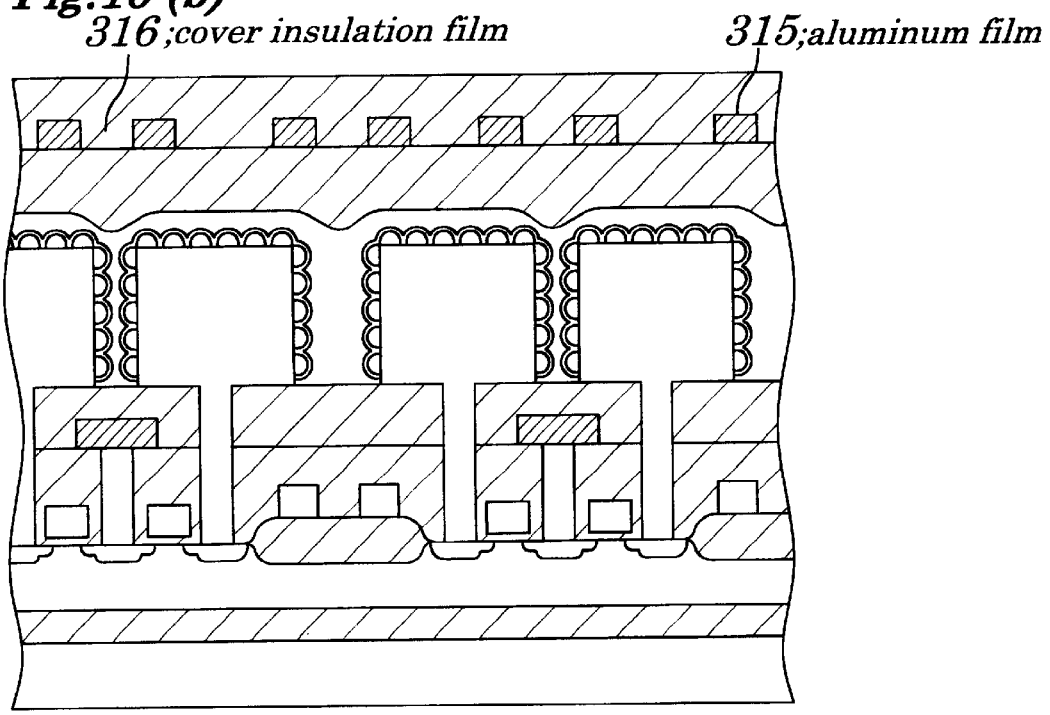
Figure 11:
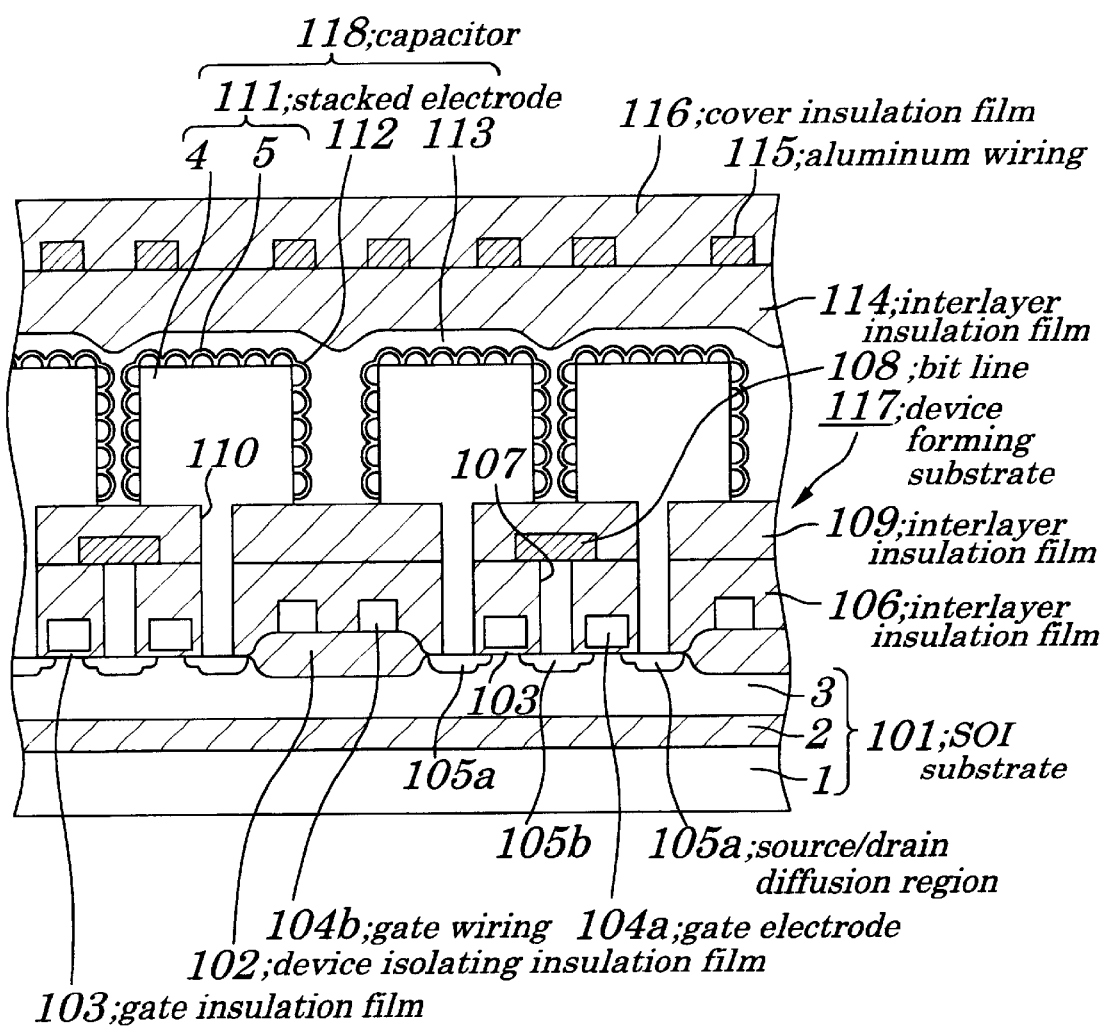
FIG. 11 shows in construction a cross-sectional view of the DRAM fabricated by the conventional method for fabricating the DRAM.

Subsequently, based on the results of monitoring as shown in FIG. 9, a value of the substrate temperature is determined so as to form the surface irregularity optimum in size on the surface of the aluminum film. Up to this value of the substrate temperature thus determined, the device forming substrate is heated. Then, the aluminum film 315 with a film thickness of 200 nm is deposited onto the interlayer insulation film 314 by using the RF sputtering process. Subsequently, as shown in FIG. 10(*a*), by using the photolithography process and the dry etching process, the aluminum film 315*a* is treated and formed into the aluminum wiring 315. After that, by using the plasma CVD process, the interlayer insulation film 316 is formed, whereby the DRAMs are produced.

As described above, in this embodiment, it suffices to tilt the sample table 401 and find out its inclination angle $\theta_c$ at which the test liquid 405 having been dropped at the surface of the test sample 407 begins to flow. Consequently, measurement of the inclination angle $\theta_c$ in this embodiment is very simple in operation. Further, since no light is used, there is no measurement error caused by reflection of light, which makes it possible to carry out a necessary measurement with sufficient accuracy not influenced by the material being applied.

Although the embodiments of the present invention have been described in detail with reference to the drawings, the present invention is not limited to these embodiments only. Any modifications and changes not departing from the spirit of the present invention are also included in the scope of the present invention. For example, as for the first embodiment, though the surface irregularity of the test specimen is evaluated by the use of the kinetic friction coefficient, it is also possible to use the static friction coefficient in addition to the kinetic friction coefficient. Further, though quartz is used in the contact surface of the trailer 203, it is also possible to use any other suitable materials such as diamond highest in hardness, organic materials low in hardness and like materials in addition to quartz. Furthermore, it is also possible to use a fingertip with which the surface is rubbed, provided that any quantitative determination of the surface irregularity is not required. Further, through the present invention is used in evaluating the degree of the surface irregularity of the a-Si film 24, it is also possible to use the present invention in evaluating the surface irregularity of any other material films such as semiconductor films, metal films, alloy films, metal silicide films insulation films, or like films.

On the other hand, in the second embodiment of the present invention described above, through the surface irregularity of the aluminum film 315*a* is evaluated, it is also possible to evaluate any other material films such as metal films, alloy films, metal silicide films, or semiconductor films in addition to the aluminum films. Further, it is also possible to evaluate the surface irregularity of insulation films. Further, through mercury is used as the test liquid 405, in measuring the surface irregularity of the aluminum film 315*a*, it is also possible to use any other suitable test liquid in addition to mercury. For example, in measuring the surface irregularity of the silicon film, preferably, pure water, or a mixture of hydrofluoric acid and water is used as the test liquid 405.

Further, when the test liquid 405 wets the sample being measured to make it difficult to carry out the measurement, it suffices to change in properties the surface into a non-wettable one. For example, it is preferable to coat the surface with a high molecular material having a suitable thickness by which the surface irregularity is not influenced.

The effect of the present invention is as follows: namely, as described above, in the present invention in construction, a force applied to the test specimen or the plate-like element 203 when the test specimen or the plate-like element 203 is moved from rest in a condition in which the surface of the test specimen is brought into contact with the contact surface of the plate-like element 203 is detected, which makes it possible to determine the friction coefficient of the surface of the test specimen or a parameter corresponding to the friction coefficient.

Since both the kinetic and the static friction coefficient vary in accordance with the degree of the surface irregularity of the test specimen, it is possible to evaluate the degree, i.e., size and density of the surface irregularity of the test specimen by measuring the friction coefficient or a parameter corresponding to the friction coefficient. Namely, it is possible to evaluate the surface irregularity in size and density of the test specimen in an easy manner by detecting the force required to move the plate-like element 203 on the surface of the test specimen and converting the thus detected force into the friction coefficient of the surface of the test specimen, or into the parameter corresponding to the friction coefficient. When the capacitor electrode is used as the test specimen, the surface irregularity of the test specimen in both size and density directly corresponds to the capacitance and the surface area of the silicon layer, which makes it possible to reproduce the capacitance of the capacitor without fail.

Further, when the conductive film or the insulation film is used as the test specimen, it is possible to evaluate the degree of the surface irregularity of the conductive film or of the insulation film. Consequently, it is possible to properly control their film forming conditions. Further, in contrast with the prior art, in the present invention, since any light is not used, there is not any measurement error caused by reflection of light, which makes it possible to realize a sufficient measurement accuracy and also makes it possible to avoid any interference caused by the material being applied. In addition, since any liquid chemicals and light are not used, it is possible to use the present invention in evaluating the surface irregularity of the semiconductor device without any fear of influence on the characteristics of the device. Consequently, it is possible to use the present invention in mass-producing the devices.

Further, according to the other construction of the present invention, it is possible to evaluate the static friction coefficient of the surface of the test specimen by: dropping off the fluid at the surface of the test specimen; tilting the test specimen; and, measuring the inclination angle of the test specimen, at which angle the fluid on the surface begins to flow. Namely, since the fluid is simply dropped off at the surface of the test specimen and then the test specimen is tilted to measure the inclination angle thereof, it is possible to evaluate the degree of the surface irregularity of the test specimen in an easy manner. In this case, when the stepping motor is used as the driving means for tilting the test specimen, the inclination angle of the test specimen can be easily determined by detecting the rotation angle of the stepping motor. Further, when the surface of the test specimen is wettable, it is difficult for the fluid having been dropped off at the surface of the test specimen to flow on such surface. Consequently, it is preferable to change in properties the surface of the test specimen into a non-wettable one by coating the surface with a high molecular material film.

It is thus apparent that the present invention is not limited to the above embodiments but maybe changed and modified without departing from the scope and spirit of the invention.

What is claimed is:

1. A method of evaluating a capacitance value of a capacitor on a semiconductor substrate, comprising the steps of:

measuring a static friction coefficient or a kinetic friction coefficient of a surface of an electrode of said capacitor formed on said semiconductor substrate; and evaluating a capacitance value of said capacitor based on the measured friction coefficient.

2. The method of evaluating a capacitance value of a capacitor on a semiconductor substrate, as set forth in claim 1, wherein:

the surface of said electrode is made up of a surface of a semiconductor film having hemispherical grains.

3. The method of evaluating a capacitance value of a capacitor on a semiconductor substrate, as set forth in claim 2, wherein said step of measuring the friction coefficient comprises the steps of:

mounting a contact surface of a plate-like element into contact with the surface of said electrode;

moving, from rest, said electrode across said plate-like element or said plate-like element across said electrode, while said contact surface of said plate-like element is in contact with said surface of said electrode; and detecting a force received by said electrode or by said plate-like element as a result of said moving, whereby a static friction coefficient or a kinetic friction coefficient in the surface of said electrode is measured.

4. The method of evaluating a capacitance value of a capacitor on a semiconductor substrate, as set forth in claim 7, wherein:

the surface of the electrode evaluated is a surface of a conductive film or of an insulation film, formed on the semiconductor substrate;

wherein said step of evaluating a capacitance value includes evaluating surface irregularity size or density.

5. The method of evaluating a capacitance value of a capacitor on a semiconductor substrate, as set forth in claim 3, wherein the force detected in said step of detecting a force received by said electrode or by said plate-like element is proportional to a force inducing movement in said step of moving, from rest, said electrode across said plate-like element or said plate-like element across said electrode.

6. The method of evaluating a capacitance value of a capacitor on a semiconductor substrate, as set forth in claim 2, wherein said step of measuring the friction coefficient comprises the steps of:

dropping a fluid onto the surface of said electrode;

tilting said electrode;

sensing when fluid begins to flow across the surface of the electrode, caused by said tilting of said electrode; and measuring an inclination angle at which said fluid begins to flow, whereby a static friction coefficient in the surface of said electrode is measured.

7. The method of evaluating a capacitance value of a capacitor on a semiconductor substrate, as set forth in claim 2, wherein:

the surface of the electrode evaluated is a surface of a conductive film or of an insulation film, formed on the semiconductor substrate;

wherein said step of evaluating a capacitance value includes evaluating surface irregularity size or density.

8. The method of evaluating a capacitance value of a capacitor on a semiconductor substrate, as set forth in claim 1, wherein said step of measuring the friction coefficient comprises the steps of:

mounting a contact surface of a plate-like element into contact with the surface of said electrode;

moving, from rest, said electrode across said plate-like element or said plate-like element across said electrode, while said contact surface of said plate-like element is in contact with said surface of said electrode; and detecting a force received by said electrode or by said plate-like element as a result of said moving, whereby a static friction coefficient or a kinetic friction coefficient in the surface of said electrode is measured.

9. The method of evaluating a capacitance value of a capacitor on a semiconductor substrate, as set forth in claim 7, wherein said step of measuring the friction coefficient comprises the steps of:

dropping a fluid onto the surface of said electrode;

tilting said electrode;

sensing when fluid begins to flow across the surface of the electrode, caused by said tilting of said electrode; and measuring an inclination angle at which said fluid begins to flow, whereby a static friction coefficient in the surface of said electrode is measured.

10. The method of evaluating a capacitance value of a capacitor on a semiconductor substrate, as set forth in claim 9, wherein:

the surface of the electrode evaluated is a surface of a conductive film or of an insulation film, formed on the semiconductor substrate;

wherein said step of evaluating a capacitance value includes evaluating surface irregularity size or density.

11. The method of evaluating a capacitance value of a capacitor on a semiconductor substrate, as set forth in claim 8, wherein:

the surface of the electrode evaluated is a surface of a conductive film or of an insulation film, formed on the semiconductor substrate;

wherein said step of evaluating a:capacitance value includes evaluating surface irregularity size or density.

12. The method of evaluating a capacitance value of a capacitor on a semiconductor substrate, as set forth in claim 8, wherein the force detected in said step of detecting a force received by said electrode or by said plate-like element is proportional to a force inducing movement in said step of moving, from rest, said electrode across said plate-like element or said plate-like element across said electrode.

13. The method of evaluating a capacitance value of a capacitor on a semiconductor substrate, as set forth in claim 1, wherein said step of measuring the friction coefficient comprises the steps of:

dropping a fluid onto the surface of said electrode;

tilting said electrode;

sensing when fluid begins to flow across the surface of the electrode, caused by said tilting of said electrode; and measuring an inclination angle at which said fluid begins to flow, whereby a static friction coefficient in the surface of said electrode is measured.

14. The method of evaluating a capacitance value of a capacitor on a semiconductor substrate, as set forth in any one of claims 13 or 6, inclusive, wherein:

the surface of the electrode evaluated is a surface of a conductive film or of an insulation film, formed on the semiconductor substrate;

wherein said step of evaluating a capacitance value includes evaluating surface irregularity size or density.

15. The method of evaluating a capacitance value of a capacitor on a semiconductor substrate, as set forth in claim 1, wherein:

the surface of the electrode evaluated is a surface of a conductive film or of an insulation film, formed on the semiconductor substrate;

wherein said step of evaluating a capacitance value includes evaluating surface irregularity size or density.

16. The method of evaluating a capacitance value of a capacitor on a or substrate, as set forth in claim 1, further comprising, before said step of measuring, the step of:

forming said electrode, comprising a step of:
forming hemispherical grains on a semiconductor film, wherein the surface of said electrode which is measured in said step of measuring is a surface of the semiconductor film having the hemispherical grains.

* * * * *